(12) United States Patent
Rambach

(10) Patent No.: US 8,318,452 B2
(45) Date of Patent: Nov. 27, 2012

(54) SOLID CULTURE MEDIUM FOR THE DETECTION AND/OR THE SPECIES DISCRIMINATION OF GLYCOPEPTIDE-RESISTANT ENTEROCOCCI

(76) Inventor: Alain Rambach, Paris (FR)

( * ) Notice: Subject to any disclaimer, the term of this patent is extended or adjusted under 35 U.S.C. 154(b) by 696 days.

(21) Appl. No.: 12/373,189

(22) PCT Filed: Jul. 10, 2007

(86) PCT No.: PCT/EP2007/057006
§ 371 (c)(1),
(2), (4) Date: Jan. 9, 2009

(87) PCT Pub. No.: WO2008/006816
PCT Pub. Date: Jan. 17, 2008

(65) Prior Publication Data
US 2009/0280524 A1 Nov. 12, 2009

(30) Foreign Application Priority Data
Jul. 10, 2006 (FR) .................................... 06 06252

(51) Int. Cl.
*C12Q 1/04* (2006.01)
*C12Q 1/18* (2006.01)
*C12N 9/00* (2006.01)

(52) U.S. Cl. ............ 435/34; 435/32; 435/183; 435/243; 435/252.1; 435/253.6

(58) Field of Classification Search .................... 435/32, 435/183, 243, 252.1, 253.6
See application file for complete search history.

(56) References Cited

U.S. PATENT DOCUMENTS

| | | | |
|---|---|---|---|
| 4,925,789 | A | 5/1990 | Edberg |
| 5,620,865 | A | 4/1997 | Chen et al. |
| 6,340,573 | B1 | 1/2002 | Armstrong et al. |
| 6,355,449 | B1 | 3/2002 | Chen et al. |
| 7,018,807 | B2 | 3/2006 | Chen et al. |
| 2005/0009132 | A1 | 1/2005 | Rambach |
| 2005/0112718 | A1 | 5/2005 | Nakano et al. |

FOREIGN PATENT DOCUMENTS

| | | |
|---|---|---|
| EP | 0 451 775 A1 | 10/1991 |
| WO | WO-98/04674 A | 2/1998 |
| WO | WO 2005/042770 A2 | 5/2005 |
| WO | WO-2006/085027 A2 | 8/2006 |
| WO | WO-2008/076452 A1 | 6/2008 |

OTHER PUBLICATIONS

Efthymiou, C.J. et al., Applied Microbiology, vol. 28, No. 3, pp. 417-422, Sep. 1974.
Edberg, Stephen C. et al., Journal of Clinical Microbiology, vol. 32, No. 9, pp. 2182-2184, Sep. 1994.
van Horn, Kenneth G. et al., Journal of Clinical Microbiology, vol. 34, No. 4, pp. 924-927, Apr. 1996.
Panosian et al., "Rapid Identification of *Streptococcus bovis* by Using Combination Constitutive Enzyme Substrate Hydrolyses", Journal of Clinical Microbiology, vol. 27, No. 8 (1989) pp. 1719-1722.

*Primary Examiner* — Rodney P. Swartz
(74) *Attorney, Agent, or Firm* — Birch, Stewart, Kolasch & Birch, LLP.

(57) ABSTRACT

The present invention relates to a solid culture medium for the detection and/or discrimination, among glycopeptide-resistant enterococci, of the groups of species *E. faecalis* and/or *E. faecium* belonging to the groups of resistance to the VanA/VanB glycopeptides, and *E. gallinarum/E. casseliflavus* belonging to the group of resistance to the VanC glycopeptides, wherein said medium comprises, in a culture medium selective for enterococci, at least one chromogenic substrate for α-glucosidase and at least one activator of a colored reaction, chosen from methyl-α-glucoside and glucosyl-α-glucoside, or polymers thereof.

20 Claims, No Drawings

SOLID CULTURE MEDIUM FOR THE DETECTION AND/OR THE SPECIES DISCRIMINATION OF GLYCOPEPTIDE-RESISTANT ENTEROCOCCI

The present invention relates to the field of medical and clinical microbiology. More particularly, the invention relates to means for the detection and/or the discrimination of bacterial species responsible for infections that, because they are resistant to one or more antibiotics, require the adaptation of therapeutic treatments.

More precisely, the present invention relates to a solid culture medium for the detection and/or the discrimination, among glycopeptide-resistant enterococci, of the groups of species E. faecalis and/or E. faecium belonging to the VanA/VanB groups of resistance to glycopeptides, and E. gallinarum/E. casseliflavus belonging to the VanC group of resistance to glycopeptides, wherein said medium comprises, in a culture medium selective for enterococci, at least one chromogenic substrate for α-glucosidase and at least one activator of a colored reaction, chosen from methyl-α-glucoside and glucosyl-α-glucoside, or polymers thereof.

Strains of vancomycin-resistant enterococci (VRE) and, more broadly glycopeptide-resistant enterococci, were first isolated clinically in the 1980s. Since, the incidence of VRE in hospital settings has continued to grow. These bacteria are generally responsible for nosocomial infections of concern to medical personnel. Moreover, the emergence of multi-resistant VRE, i.e., enterococci resistant not only to vancomycin but also to one or more non-glycopeptide antibiotics, is a genuine therapeutic issue for clinicians. Indeed, the multiplicity and the dissemination of resistance characteristics between strains of enterococci have made some invulnerable to standard therapies.

Unlike mechanisms that confer resistance to most families of antibiotics, glycopeptide resistance does not depend on the product of a single gene but requires the regulated and interactive expression of a set of closely associated genes: van glycopeptide resistance operons.

To date, several types (or groups) of glycopeptide resistance have been identified among enterococci, among which VanA (vanA operon), VanB (vanB operon) and VanC (vanC operon) are the types most frequently encountered (see Table I below). Some of these groups of genes are transmissible between bacterial strains (so-called acquired resistance), whereas others are intrinsic and non-transmissible (Table I).

Ultimately, among VRE, the most frequent species of enterococci can be generally divided into species or groups of species more specifically associated with a given type of glycopeptide resistance (Table I).

TABLE I

| Type of glycopeptide resistance | Species of enterococci | Origin of resistance genes |
|---|---|---|
| VanA | E. faecium, E. faecalis | acquired |
| VanB | E. faecium, E. faecalis | acquired |
| VanC | E. gallinarum, E. casseliflavus | intrinsic |

As shown in Table II below, the types of glycopeptide resistance among enterococci are distinguished not only by the genetic sequences responsible (sequences of van operons), their carrier (plasmid or chromosome) and the mechanisms of expression and regulation of expression involved (inducible or constitutive resistance), but also by associated levels of glycopeptide resistance.

TABLE II

| Type of glycopeptide resistance | MIC | |
|---|---|---|
| | Vancomycin | Teicoplanin |
| VanA | 64 –> 1024 | 16 –> 512 |
| VanB | 4 –> 1024 | 0.5-1 |
| VanC | 2 –> 32 | 0.5-1 |

MIC: minimum inhibitory concentration in mg/l

In order to detect and/or discriminate bacteria, methods based on detecting phenotypic or genotypic characters are commonly used. Moreover, several of these methods can be combined advantageously to increase the discriminating power of the analysis by improving detection selectivity and/or sensitivity and/or specificity.

In the particular field of VRE detection, a known phenotypic method makes it possible to discriminate, by specific coloring, VanC VRE cultures and non-VanC VRE cultures (which are not colored). This method, implemented in a liquid medium (test tubes or wells), uses acidification of the medium related to the presence of methyl-α-glucoside. In this test, the sugar is used at a concentration of 20 g/l, in the presence of a pH indicator used to indicate acidification of the medium.

However, the discriminating power of this test still needs to be improved, in terms of both selectivity and specificity, on the one hand in order to eliminate the false-positive or false-negative results likely to be obtained, and on the other hand in order to enable detection of VRE on the species level, which is impossible with the current test.

Thus, currently there is a need for a detection test for the VRE most frequently encountered in a clinical setting, one which is simultaneously simple, fast, sensitive, selective, specific and reliable, to enable the discriminating detection of VRE on the species level and on the level of the associated type of glycopeptide resistance.

It is precisely to this need that the present invention responds by providing phenotypic means that can be utilized in a solid medium (on plates) for the effective and discriminating detection of VRE.

In this respect, it should be noted that, as shown in the example and in Table III below, the test tube technique of the prior art, if applied as-is in a solid medium, leads to only slight coloring of colonies, which thus does not make it possible to discriminate or differentiate VRE.

In addition, it is shown herein (see Table III below) that a chromogenic substrate used in a solid medium does not, in and of itself, enable satisfactory detection of VRE.

The results reported within the framework of the invention show that the combination in a test tube of methyl-α-glucoside and a pH indicator cannot be simply replaced, in a solid medium, by a chromogenic substrate for α-glucosidase, contrary to what a person skilled in the art might expect on the basis of the likely hypothesis that detection was achieved by simply demonstrating the presence or absence of the gene coding for the α-glucosidase enzyme.

Moreover, the present invention shows that various combinations of at least two substrates for α-glucosidase, of which one is chromogenic, lead, in a solid medium, to quite unexpected results insofar as coloring is reversed according to the substrates used and to the combinations thereof. It should be noted also that α-glucosidase substrates other than those explicitly described below were tested by the Inventor without success. For example, in contrast to maltose as noted below, trehalose does not yield satisfactory results in terms of the detection and differentiation of VRE species or groups of species (data not shown).

Finally, the results obtained within the framework of the invention are not only surprising and unexpected, but are also particularly advantageous because they enable discriminating detection of VanC VRE with respect to VanA/VanB VRE (and vice versa), or the species *E. faecalis* or the species *E. faecium* with respect to other VRE species.

Thus, a first aspect of the present invention relates to a solid culture medium for the detection and/or the discrimination of groups of glycopeptide-resistant species of enterococci:

*E. faecalis* and/or *E. faecium*, belonging to the VanA/VanB groups of resistance to glycopeptides; and

*E. gallinarum/E. casseliflavus*, belonging to the VanC group of resistance to glycopeptides, wherein said medium comprises, in a culture medium selective for enterococci, at least one chromogenic substrate for α-glucosidase and at least one activator of a colored reaction, chosen from methyl-α-glucoside or polymers thereof and glucosyl-α-glucoside or polymers thereof.

The use, in a solid medium, of a chromogenic substrate for α-glucosidase associated with at least one activator of a colored reaction, such as that described for the first time herein, notably has the advantage of enabling the development of solid media that make possible the differentiation of VRE species or groups of species upon isolation, without having to perform additional tests.

Herein, "methyl-α-glucoside polymers" refer to oligosaccharides and polysaccharides that are adapted for use in a solid bacterial culture medium and that release, after breaking of the glycosidic bonds (for example, by enzymatic degradation), methyl-α-glucoside. A typical example of one such polymer is methyl-α-maltoside.

Herein, "glucosyl-α-glucoside polymers" refer to oligosaccharides and polysaccharides that are adapted for use in a solid bacterial culture medium and that release, after breaking of the glycosidic bonds (for example, by enzymatic degradation), glucosyl-α-glucoside, more commonly called maltose.

An "activator of a colored reaction" is, within the scope of the present invention, a compound whose function is to improve the quality of the reaction observed. This compound is chosen from methyl-α-glucoside or polymers thereof and glucosyl-α-glucoside or polymers thereof. As the results presented in Table III indicate (see the example below), the presence in the inventive solid culture medium of at least one activator of a colored reaction is essential for the discriminating detection of VRE species or groups of species.

The present invention thus enables the detection and, advantageously, the identification on the species level or on the group of species level of a colored colony of VRE, even in the presence of thousands of other colonies likely to develop on the inventive selective solid medium. In fact, the VRE colonies detected by the inventive medium are colored by a certain color whereas the other microorganisms display different colors or are colorless.

Moreover, the detection of VRE colonies is, within the framework of the present invention, direct in the sense that it requires no act or intervention, such as the use of a developing solution or of a particular light source, subsequent to the culturing of the bacteria.

According to one embodiment, the inventive culture medium comprises at least one chromogenic substrate for α-glucosidase and methyl-α-glucoside or a polymer thereof, used as an activator of a colored reaction at a concentration of at least 10 g/l approximately, for the detection and/or the discrimination by coloring of the species *E. gallinarum/E. casseliflavus* belonging to the VanC group of resistance to glycopeptides. Under these conditions, it is by the quite particular and specific coloring of the colonies of *E. gallinarum/E. casseliflavus* that differentiation is made possible. This coloring, generated by the chromogenic substrate, will only relate to colonies of *E. gallinarum/E. casseliflavus*, hence the concept of coloring specificity.

Preferably, the concentration of methyl-α-glucoside in the medium is at least 20 g/l approximately. More preferably, this concentration is 20 g/l approximately.

According to another embodiment, the inventive culture medium comprises at least one chromogenic substrate for α-glucosidase and glucosyl-α-glucoside (maltose) or a polymer thereof, used as an activator of a colored reaction at a concentration of at least 0.1 g/l approximately, for the detection and/or the discrimination by coloring of the species *E. faecalis* belonging to the VanA/VanB groups of resistance to glycopeptides. Here, only colonies of the strains of the species *E. faecalis* are of the color generated by the chromogenic substrate on the plates.

Preferably, the concentration of maltose in the medium is at least 0.2 g/l approximately. More preferably, this concentration is 0.2 g/l approximately.

According to still another embodiment, the inventive culture medium comprises at least one chromogenic substrate for α-glucosidase and, as activators of a colored reaction, methyl-α-glucoside or a polymer thereof, used at a concentration of at least 10 g/l approximately, and glucosyl-α-glucoside or a polymer thereof, used at a concentration of at least 0.1 g/l approximately, for the detection and/or the discrimination by the absence of coloring of the species *E. faecium* belonging to the VanA/VanB groups of resistance to glycopeptides. In this case, the colonies of strains of the species *E. faecalis* and *E. gallinarum/E. casseliflavus* are colored by virtue of the chromogenic substrate on the plates. Only the colonies of strains of *E. faecium* are not colored by virtue of this substrate, which enables a qualified differentiation "by lack of coloring," i.e., by the absence of the coloring generated by the chromogenic substrate, given that the colonies of *E. faecium* will appear with a different color if one or more of the other coloring components are added in the medium.

Preferably, the concentrations of methyl-α-glucoside and maltose in the medium are, respectively, at least 20 g/l approximately and at least 0.2 g/l approximately. More preferably, these concentrations are, respectively, 20 g/l approximately and 0.2 g/l approximately.

Thus, according to the embodiments implemented, the inventive culture medium makes it possible to easily discriminate a VRE species or group of species by the single coloring, the differential coloring or the absence of coloring of the colonies present on the solid culture medium.

The "selective culture medium for enterococci" comprises various selective factors for enterococci familiar to those skilled in the art. For example, inhibitors of Gram-negative bacteria make it possible to improve the properties of the culture medium and to more easily isolate enterococci (Gram-positive bacteria).

Moreover, in order to optimize the results provided by the inventive culture medium, it may be important to add factors known to be selective for VRE; such factors will make it possible to obtain a solid culture medium specific for VRE. Preferably, such a selective and specific medium for VRE comprises at least one glycopeptide antibiotic.

In one embodiment, said glycopeptide antibiotic is chosen from vancomycin, teicoplanin and combinations thereof.

Advantageously, vancomycin is used at a concentration from 2 mg/l to 15 mg/l approximately, preferably at a concentration from 3 mg/l to 9 mg/l approximately, more preferably at a concentration from 4 mg/l to 8 mg/l approximately, with a particularly preferred value of 6 mg/l approximately.

Teicoplanin is used at a concentration from 0.5 mg/l to 16 mg/l approximately, preferably at a concentration from 1 mg/l to 10 mg/l approximately, more preferably at a concentration from 2 mg/l to 8 mg/l approximately, with a particularly preferred value of 5 mg/l approximately.

Of course, those skilled in the art are in all cases able to determine and, if necessary, to test the concentrations or ranges of concentrations of the glycopeptide(s) suited for implementing the present invention (based on their general knowledge, based on the literature and/or based on Table II above).

The chromogenic substrate for α-glucosidase preferably comprises a precipitable chromophore, which is released by the hydrolysis of the substrate by its enzyme. Thus, the bacterial colony is colored according to the chromophore released. Since the chromophore released in the culture medium is solid, it thus remains near the colony from which it was released.

Preferably, said chromophore is chosen from the indoxyl, halogen indoxyl (bromo-indoxyl, chloro-indoxyl, fluoro-indoxyl, iodo-indoxyl, dichloro-indoxyl, chloro-bromo-indoxyl, tri-chloro-indoxyl), methyl-indoxyl or hydroxyquinoline derivatives. Particularly preferred derivatives are chosen from the following derivatives: 6-chloro-indoxyl, 5-bromo-indoxyl, 3-bromo-indoxyl, 6-fluoro-indoxyl, 5-iodo-indoxyl, 4,6-dichloro-indoxyl, 6,7-dichloro-indoxyl, 5-bromo-4-chloro-indoxyl, 5-bromo-6-chloro-indoxyl, 4,6,7-trichloro-indoxyl, N-methyl-indoxyl and 8-hydroxyquinoline.

More preferentially, the chromogenic substrate for α-glucosidase is a 5-bromo-4-chloro-indoxyl-α-glucoside.

The chromogenic substrate is typically used at a concentration from 0.01 g/l to 0.5 g/l approximately. A preferred concentration is 0.1 g/l approximately.

It is specified that the chromogenic substrate present in the inventive culture medium can be replaced, or combined, with at least one fluorogenic substrate. This substrate is formed by coupling a substrate for α-glucosidase with a fluorophore such as 4-methyl umbelliferyl.

A second aspect of the present invention relates to the use of a culture medium as defined above, for the detection and/or the discrimination of the groups of glycopeptide-resistant species of enterococci:

E. faecalis and/or E. faecium, belonging to the VanA/VanB groups of resistance to glycopeptides; and E. gallinarum/E. casseliflavus, belonging to the VanC group of resistance to glycopeptides.

A third aspect of the invention relates to a method for the detection and/or the discrimination, in a sample, of groups of glycopeptide-resistant species of enterococci:

E. faecalis and/or E. faecium, belonging to the VanA/VanB groups of resistance to glycopeptides; and E. gallinarum/E. casseliflavus, belonging to the VanC group of resistance to glycopeptides, characterized in that it comprises at least the following steps:

a) inoculation of a culture medium as defined above, with said sample or an inoculum derived therefrom;

b) detection, on said culture medium, of the presence of groups of glycopeptide-resistant species of enterococci E. faecalis/E. faecium and E. gallinarum/E. casseliflavus; and c) optionally, differentiation of the species E. faecalis and/or E. faecium and/or E. gallinarum/E. casseliflavus from other microorganisms present on said culture medium.

Use of the inventive culture medium advantageously can be preceded by an enrichment step carried out using methods known to those skilled in the art. In particular, alkaline peptone water with 1 g/l NaCl (pH 8.6) or 3 g/l NaCl can be used.

The object of the present invention is not limited to the description above. Other embodiments and advantages of the present invention will arise from the example below, provided here on a purely illustrative basis. It is clear that neither the object nor the scope of the present invention is limited by this example.

EXAMPLE

A) Solid Culture Medium Base (in g/l)

Peptone 10

Yeast extract 5

Agar 15

B) Glycopeptides several series of experiments were conducted: certain series were implemented on a medium selective for enterococci (free of glycopeptides), others on a medium selective for VRE, containing 6 mg/l of vancomycin. The results presented in Table III below reflect the mean results obtained over all series.

C) Other Ingredients (in g/l)

See Table III below.

X-α-glucoside: chromogenic substrate for α-glucosidase.

The results presented in Table III below were obtained after inoculating bacteria on the culture media indicated, followed in all cases by an incubation of approximately 24 hours at approximately 37° C.

TABLE III

| | | α-GLUCOSIDASE SUBSTRATE(S) PRESENT IN THE MEDIUM | VanA/VanB | | VanC | | |
|---|---|---|---|---|---|---|---|
| | | | E. faecium | E. faecalis | E. casseliflavus | E. gallinarum | RESULTS |
| TEST TUBE CONTROLS | Known technique | 20 g/l methyl-α-glucoside + pH indicator | – | – | +/– | + | Discriminating detection of VanC versus non-VanC |

TABLE III-continued

| α-GLUCOSIDASE SUBSTRATE(S) PRESENT IN THE MEDIUM | | VanA/VanB | | VanC | | RESULTS |
|---|---|---|---|---|---|---|
| | | E. faecium | E. faecalis | E. casseliflavus | E. gallinarum | |
| TESTS ON PLATES | Extension of the known technique | 20 g/l glucosyl-α-glucoside (maltose) + pH indicator | + | + | + | + | No discrimination neither between species nor between groups of resistance |
| | 20 g/l methyl-α-glucoside + pH indicator | | − | − | − | − | Mediocre or no discrimination, above all for strains difficult to grow |
| | 0.1 g/l x-α-glucoside | | − | +/− | − | − | Mediocre or no discrimination between species between groups of resistance |
| | 0.1 g/l X-α-glucoside 0.2 g/l glucosyl-α-glucoside (maltose) | | − | ++ | − | − | Discriminating detection of the species E. faecalis |
| | 0.1 g/l X-α-glucoside 0.1 g/l methyl-α-glucoside | | − | −/+ | − | − | Mediocre or no discrimination between species between groups of resistance |
| | 0.1 g/l X-α-glucoside 1 g/l methyl-α-glucoside | | − | +/− | ++ | + | Detection of VanC but insufficiently discriminating |
| | 0.1 g/l X-α-glucoside 20 g/l methyl-α-glucoside | | − | − | + | + | Discriminating detection of VanC versus non-VanC |
| | 0.1 g/l X-α-glucoside 20 g/l methyl-α-glucoside 0.2 g/l glucosyl-α-glucoside (maltose) | | − | ++ | ++ | + | Discriminating detection of the species E. faecium |

+: intensity of coloring
−: no coloring

The invention claimed is:

1. A solid culture medium for the detection and/or the discrimination of groups of glycopeptide-resistant species of enterococci:

E. faecalis and/or E. faecium, belonging to the VanA/VanB groups of resistance to glycopeptides; and E. gallinarum/E. casseliflavus, belonging to the VanC group of resistance to glycopeptides, wherein said medium comprises, in a culture medium selective for enterococci, at least one chromogenic substrate for α-glucosidase and at least one activator of a colored reaction, chosen from the group consisting of methyl-α-glucoside, polymers of methyl-α-glucoside, glucosyl-α-glucoside and polymers of glucosyl-α-glucoside; wherein reaction of said substrate with said α-glucosidase results in a color that allows for detection and/or the discrimination of E. faecalis and/or E. faecium, belonging to the VanA/VanB groups of resistance to glycopeptides and E. gallinarum/E. casseliflavus, belonging to the VanC group of resistance to glycopeptides.

2. The culture medium of claim 1, wherein said culture medium comprises at least one chromogenic substrate for α-glucosidase and methyl-α-glucoside or a polymer thereof, used at a concentration of at least 10 g/l approximately, for the detection and/or the discrimination of the species E. gallinarum/E. casseliflavus belonging to the VanC group of resistance to glycopeptides.

3. The culture medium of claim 1, wherein said culture medium comprises at least one chromogenic substrate for α-glucosidase and glucosyl-α-glucoside or a polymer thereof, used at a concentration of at least 0.1 g/l approximately, for the detection and/or the discrimination of the species E. faecalis belonging to the groups of resistance to VanA/VanB glycopeptides.

4. The culture medium of claim 1, wherein said culture medium comprises at least one chromogenic substrate for α-glucosidase, methyl-α-glucoside or a polymer thereof, used at a concentration of at least 10 g/l approximately, and glucosyl-α-glucoside or a polymer thereof, used at a concentration of at least 0.1 g/l approximately, for the detection and/or the discrimination of the species E. faecium belonging to the groups of resistance to VanA/VanB glycopeptides.

5. The culture medium according to claim 1, wherein said culture medium selective for enterococci is a medium selective for glycopeptide-resistant enterococci comprising at least one glycopeptide antibiotic.

6. The culture medium of claim 5, wherein said glycopeptide antibiotic is chosen from the group consisting of vancomycin, teicoplanin and combinations thereof.

7. The culture medium of claim 6, wherein vancomycin is used at a concentration from 2 mg/l to 15 mg/l approximately.

8. The culture medium of claim 6, wherein the teicoplanin is used at a concentration from 0.5 mg/l to 16 mg/l approximately.

9. The culture medium according to claim 1, wherein said chromogenic substrate releases, by hydrolysis, a precipitable chromophore chosen from the group consisting of the indoxyl, halogen indoxyl, methyl-indoxyl and hydroxyquinoline derivatives.

10. The culture medium according to claim 1, wherein said chromogenic substrate for α-glucosidase is a 5-bromo-4-chloro-indoxyl-α-glucoside.

11. The culture medium of claim 7, wherein vancomycin is used at a concentration from 3 mg/l to 9 mg/l approximately.

12. The culture medium of claim 11, wherein vancomycin is used at a concentration from 4 mg/l to 8 mg/l approximately.

13. The culture medium of claim 12, wherein vancomycin is used at a concentration of 6 mg/l approximately.

14. The culture medium of claim 8, wherein teicoplanin is used at a concentration from 1 mg/l to 10 mg/l approximately.

15. The culture medium of claim 14, wherein teicoplanin is used at a concentration from 2 mg/l to 8 mg/l approximately.

16. The culture medium of claim 15, wherein teicoplanin is used at a concentration of 5 mg/l approximately.

17. The culture medium of claim 9, wherein said halogen indoxyl derivatives are chosen from the group consisting of bromo-indoxyl, chloro-indoxyl, fluoro-indoxyl, iodo-indoxyl, dichloro-indoxyl, chloro-bromo-indoxyl, and trichloro-indoxyl derivatives.

18. The culture medium of claim 9, wherein said precipitable chromophore is chosen from the group consisting of the following derivatives: 6-chloro-indoxyl, 5-bromo-indoxyl, 3-bromo-indoxyl, 6-fluoro-indoxyl, 5-iodo-indoxyl, 4,6-dichloro-indoxyl, 6,7-dichloro-indoxyl, 5-bromo-4-chloro-indoxyl, 5-bromo-6-chloro-indoxyl, 4,6,7-trichloro-indoxyl, N-methyl-indoxyl, and 8-hydroxy-quinoline.

19. A method for the detection and/or the discrimination, in a sample, of groups of glycopeptide-resistant species of enterococci:

E. faecalis and/or E. faecium, belonging to the VanA/VanB groups of resistance to glycopeptides; and E. gallinarum/E. casseliflavus, belonging to the VanC group of resistance to glycopeptides, wherein it comprises at least the following steps:

a) inoculation of a culture medium as defined in claim 1 with said sample or an inoculum obtained from said sample;

detection on said culture medium of the presence of groups of glycopeptide-resistant species of enterococci E. faecalis/E. faecium and E. gallinarum/E. casseliflavus; wherein said culture medium is selective for enterococci and comprises at least one chromogenic substrate for α-glucosidase and at least one activator of a colored reaction, chosen from the group consisting of methyl-α-glucoside, polymers of methyl-α-glucoside, glucosyl-α-glucoside and polymers of glucosyl-α-glucoside; wherein reaction of said substrate with said α-glucosidase results in a color that allows for detection and/or the discrimination of E. faecalis and/or E. faecium, belonging to the VanA/VanB groups of resistance to glycopeptides and E. gallinarum/E. casseliflavus, belonging to the VanC group of resistance to glycopeptides.

20. The method of claim 19, further comprising the following step:

c) differentiation of the species E. faecalis and/or E. faecium and/or E. gallinarum/E. casseliflavus from other microorganisms present on said culture medium.

\* \* \* \* \*